United States Patent [19]
Perrault et al.

[11] Patent Number: 6,039,940
[45] Date of Patent: Mar. 21, 2000

[54] INHERENTLY ANTIMICROBIAL QUATERNARY AMINE HYDROGEL WOUND DRESSINGS

[75] Inventors: James J. Perrault, Vista, Calif.; Cameron G. Rouns, Pocatello, Id.

[73] Assignee: Ballard Medical Products, Draper, Utah

[21] Appl. No.: 09/144,727

[22] Filed: Sep. 1, 1998

Related U.S. Application Data

[63] Continuation-in-part of application No. 08/738,651, Oct. 28, 1996, Pat. No. 5,800,685.

[51] Int. Cl.$^7$ .......................... A61K 31/785; A61F 13/00
[52] U.S. Cl. ..................... 424/78.06; 424/78.08; 424/78.35; 424/78.37; 424/443; 424/445
[58] Field of Search ...................................... 424/443, 445, 424/78.06, 78.07, 78.08, 78.35, 78.37

[56] References Cited

U.S. PATENT DOCUMENTS

| | | |
|---|---|---|
| 3,898,188 | 8/1975 | Rembaum et al. . |
| 3,975,350 | 8/1976 | Hudgin et al. . |
| 4,119,094 | 10/1978 | Micklus et al. . |
| 4,191,743 | 3/1980 | Klemm et al. . |
| 4,226,232 | 10/1980 | Spence . |
| 4,318,947 | 3/1982 | Joung . |
| 4,373,009 | 2/1983 | Winn . |
| 4,393,048 | 7/1983 | Mason, Jr. et al. . |
| 4,515,593 | 5/1985 | Norton . |
| 4,563,184 | 1/1986 | Korol . |
| 4,570,629 | 2/1986 | Widra . |
| 4,657,006 | 4/1987 | Rawlings et al. . |
| 4,705,709 | 11/1987 | Vailancourt . |
| 4,728,323 | 3/1988 | Matson . |
| 4,769,013 | 9/1988 | Lorenz et al. . |
| 4,791,063 | 12/1988 | Hou et al. . |
| 5,004,760 | 4/1991 | Patton et al. .......................... 424/78.27 |
| 5,006,267 | 4/1991 | Vaughn et al. .......................... 210/755 |
| 5,019,096 | 5/1991 | Fox, Jr. et al. . |
| 5,069,907 | 12/1991 | Mixon et al. . |
| 5,082,697 | 1/1992 | Patton et al. .......................... 427/340 |
| 5,269,770 | 12/1993 | Conway et al. . |
| 5,432,000 | 7/1995 | Young, Sr. et al. . |
| 5,498,478 | 3/1996 | Hansen et al. . |
| 5,512,329 | 4/1996 | Guire et al. . |
| 5,563,056 | 10/1996 | Swan et al. . |
| 5,599,321 | 2/1997 | Conway et al. . |
| 5,624,704 | 4/1997 | Darouiche et al. . |
| 5,670,557 | 9/1997 | Dietz et al. . |
| 5,674,561 | 10/1997 | Dietz et al. . |
| 5,800,685 | 9/1998 | Perrault . |

FOREIGN PATENT DOCUMENTS

| | | |
|---|---|---|
| 92/06694 | 4/1992 | WIPO . |
| WO 97/14448 | 4/1997 | WIPO . |

OTHER PUBLICATIONS

I. I. Raad, "Vascular Catheters Impregnated with Antimicrobial Agents: Present Knowledge and Future Direction," *Infection Control and Hospital Epidemiology*, 18(4): 227–229 (1997).

R. O. Darouiche, H. Safar, and I. I. Raad, "In Vitro Efficacy of Antimicrobial–Coated Bladder Catheters in Inhibiting Bacterial Migration along Catheter Surface," *J. Infect. Dis.*, 176: 1109–12 (1997).

W. Kohen and B. Jansen, "Polymer Materials for the Prevention of Catheter–related Infections," *Zbl. Bakt.*, 283: 175–186 (1995).

*Primary Examiner*—Robert H. Harrison
*Attorney, Agent, or Firm*—Locke Liddell & Sapp LLP

[57] ABSTRACT

A composition and method for treating a wound with an inherently antimicrobial dressing. The dressing is a hydrogel containing from about 15 to 95 percent, and preferably from about 61 to 90 percent, by weight of a cationic quaternary amine acrylate polymer prepared by the polymerization of acryloyloxyethyl(or propyl)-trialkyl(or aryl)-substituted ammonium salts or acrylamidoethyl(or propyl)-trialkyl(or aryl)-substituted ammonium salts. The antimicrobial hydrogels are non-irritating to the wound, absorb wound exudate, and, due to the inherently antimicrobial properties, enhance the sterile environment around the wound. The hydrogels have sufficient adhesive properties that loose contact with the wound is assured but can also be removed without leaving any gel residue on the wound. The wound dressings are preferably formed on a substrate, such as a web or patch, for ease in application to and removal from the wound. If desired, additional antimicrobial or other pharmaceutically active agents can also be incorporated into the hydrogel structure.

15 Claims, No Drawings

INHERENTLY ANTIMICROBIAL QUATERNARY AMINE HYDROGEL WOUND DRESSINGS

This application is a continuation-in-part of application Ser. No. 08/738,651 filed Oct. 28, 1996 and issued Sep. 1, 1998 as U.S. Pat. No. 5,800,685.

This invention is drawn to hydrogel wound dressings that are inherently antimicrobial. More particularly, this invention is drawn to inherently antimicrobial hydrogels containing wound dressings wherein the hydrogel is formed by the polymerization of acrylated quaternary ammonium monomers in an aqueous media.

In the past, wounds have been treated with antimicrobial active agents applied to the wound and covered with a covering that inhibits the healing process. For example, it was conventional practice early in the 20th Century to apply an antiseptic mercury agent such at thimerosal (Merthiolate) or merbromin (Mercurochrome) and the like to a wound and then cover or wrap the wound with a bandage such as gauze or an adhesive strip having a central absorbent gauze portion.

A disadvantage of this approach is that the wound often weeps or exudes fluids such as blood, pustulation and the like. While the gauze may absorb some of these fluids, the gauze often adheres to the wound such that removal of the dressing reopens the wound.

Advances in the art have been made in both bandages and antimicrobial agents. Certain bandages now contain a non-adhering polymeric coating over or, in place of, the gauze that inhibits the adhering of the absorbent material to the wound but also inhibits the absorption of the exudate that is necessary to properly heal the wound.

Certain wound dressing materials have been used to absorb exudate and promote healing. For example, Mason, et al., U.S. Pat. No. 4,393,048 teaches a hydrogel composition which, when applied as a powder, absorbs wound exudate. The hydrogel formation may not be complete and lumps of partially hydrated powders form which, when removed, may reopen the wound.

It is known that wounds heal more rapidly and completely if kept in a slightly moist or hydrated state. Polyethylene glycol containing hydrogel wound coverings are disclosed in Spence, U.S. Pat. No. 4,226,232. These hydrogels cannot be sterilized by irradiation due to the formation of free radicals.

Rawlings et al., U.S. Pat. No. 4,657,006, illustrate wound dressings comprised of a hydrophilic polymer having moisture and vapor permeability properties. However, the exudate absorbed by the hydrophilic polymer tends to harden or solidify the polymer.

An ideal wound dressing should not only absorb exudate but also possess antimicrobial properties. For example, Matson, U.S. Pat. No. 4,728,323 discloses a wound dressing comprising a substrate coated with an antimicrobial coating of a silver salt that allegedly keeps the wound moist.

Korol, U.S. Pat. No. 4,563,184, discloses wound dressings comprising a polymer, such as poly(2-hydroxyethylmethacrylate), a solvent, such as polyethylene glycol, and a plasticizer such as DMSO. An antimicrobial agent, such as silver sulfadiazine, may be incorporated into the polymeric material.

Widra, U.S. Pat. No. 4,570,629, is drawn to absorbent hydrogel membrane wound dressings made up of hydrophilic biopolymeric copolyelectrolytes comprising a water-soluble linear anionic protein polyelectrolyte component derived from keratin and a water-soluble linear cationic biopolymer polyelectrolyte component derived from either collagen or a glucosamineglycan. The membranes may also contain antibiotics.

Klemm et al., U.S. Pat. No. 4,191,743, teache the administration of antibiotics to wounds using a wound dressing comprising at least two layers of synthetic resin arranged one above the other having an intermediate layer composed of a synthetic resin granulate having an antibiotic incorporated therein.

It is known that certain quaternary amine salts possess antimicrobial properties. Examples include benzethonium chloride and benzalkonium chloride (Bactine®). It is also known that certain quaternary amines can be incorporated into polymeric substrates to provide a certain degree of antimicrobial activity.

Rebaum et al., U.S. Pat. No. 3,898,188, teach cationic polyelectrolytes homopolymers formed from an alkyl amine halide monomer that are useful for various medical applications. These polymers are formed by the head-to-tail quaternization reaction of the monomer to form linear chains. Such polyelectrolyte homopolymers are taught to possess bacteriocidal activity and can be topically applied to traumatic skin areas such as in the treatment of burns, abrasions or cuts. However, the homopolymers do not possess gel forming capabilities and, in order to form a moisture retaining structure, must be combined with a polyvinyl alcohol or polyvinyl pyrrolidone polymer. Such combinations result in films that can impregnate gauze materials to form an antiseptic or germicidal dressing material. The homopolymers may also be converted to branch polymers having a comb-like structure by attaching the quaternary homopolymer to the backbone of a polymeric substrate such as a poly-dialkylaminoalkylacrylates or a polyalkylaminoacrylamides. Such comb-like polymers are useful for coating onto substrates such as photocopy paper. Further, the polyelectrolyte monomers can be copolymerized with anionic polymers such as polystyrene sulfonates, polyacrylates or heparin to provide copolymers that can coat surfaces such as tubes, catheters, valves and the like with a non-thrombogenic coating.

Hou et al., U.S. Pat. No. 4,791,063, teach polyionene-transformed modified polymer-polysaccharide separation matrices for use in removing contaminants of microorganism origin from biological liquids. This patent teaches that absorption of bacterial cells by ion-exchange resins is attributable to electrostatic attraction between quaternary ammonium groups on the resin surface and carboxyl groups on the bacteria cell surface.

Hansen et al., U.S. Pat. No. 5,498,478 is directed to the use of a polyethylene glycol or similar polymer as a binder material for fibers of any variety. The binder and fibers may be pretreated by slurrying the fibers in baths containing antimicrobial agents as part of the solution, thereby causing the fibers and the subsequently formed matrix of polymer and fibers to have an antimicrobial ability.

Mixon et al., U.S. Pat. No. 5,069,907 is directed to the formation and use of a polymeric sheet which may include an antimicrobial agent. This patent teaches of the inclusion of antimicrobial agents into either a pressure-sensitive layer, such as an adhesive, or in a drape used to cover a wound or other sensitive area.

Dietz et al., U.S. Patents 5,674,561 and 5,670,557 are directed to polymerized microemulsion pressure sensitive adhesive compositions that may optionally contain antimicrobial and/or other biologically active agents. The potential antimicrobial activity of quaternary amine and quaternary ammonium salts is taught. It is further taught that an antimicrobial agent can be added so as to be contained in a specific layer of a pressure sensitive adhesive device for use as a medical skin covering and/or as a wound dressing.

Young et al., U.S. Pat. No. 5,432,000, teach the use of a polymeric network for adhering particulate materials to a fiber or fibrous product. Specifically, this patent teaches of the use of polymers, such as polyethylene glycol or polyethylene to cause the binding of particulate materials to a fiber, such as cloth. One such particulate member which could be adhered to cloth is an antimicrobial agent, such as epoxide phenol or another antimicrobial substance.

There is a need for a wound dressing that incorporates the desired properties of exudate absorption, moisture retention to the wound and antimicrobial properties into a single hydrogel structure. Such has not been previously demonstrated in the prior art.

OBJECTS AND SUMMARY OF THE INVENTION

It is therefore an object of the present invention to provide a cationic quaternary amine polyacrylate hydrogel wound dressing that is inherently antimicrobial.

Another object of this invention is to provide a hydrogel wound dressing that absorbs wound exudate and allows the wound to remain in a hydrated or moist occlusive condition.

A still further object of the invention is to provide a hydrogel formed from the polymerization of cationic quaternary amine acrylic acid ester or amide monomers wherein the formed polymers are inherently antimicrobial and, when hydrated, provide hydrogel dressings having an adhesive quality that loosely adheres to the wound to keep the wound hydrated, absorb exudate and yet is readily removed without aggravating the wound healing process.

Another object of the invention is to provide a method for treating wounds by applying to the wound an inherently antimicrobial cationic quaternary amine containing polyacrylate hydrogel to promote healing, absorb exudate and retain the wound in a moist or hydrated condition.

These and other objects are accomplished by means of an aqueous hydrogel composition comprising between about 15 to 95% by weight of a cationic quaternary ammonium polyacrylate polymer of following Formula I:

FORMULA I

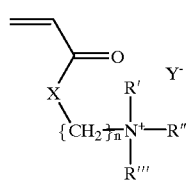

wherein n is an integer of 2 to 3; R', R" and R'" are independently selected from the group consisting of H, $C_1$ to $C_{16}$ alkyl, aryl, arylamine, alkylamine, alkaryl and aralkyl; X is selected from the group consisting of O and NH; $Y^-$ is an acceptable anionic counterion to the $N^+$ of the quaternary amine and m is an integer greater than 50,000.

Alkyl groups are preferably lower alkyl, of C, to $C_8$ with methyl or ethyl groups being particularly preferred. Aryl is preferably phenyl but can be any suitable aromatic moiety such as those selected from the group consisting of phenyl, thiophenyl, naphthyl, biphenyl, pyridyl, pyrimidinyl, pyrazyl, pyridazinyl, furyl, thienyl, pyrryl, quinolinyl and bipyridyl and the like. Representative of an aralkyl grouping is benzyl and representative of an alkaryl grouping is tolyl.

X is preferably O or NH. Representative of counterions represented by $Y^-$ are members selected from the group consisting of $Cl^-$, $Br^-$, $HSO_4^-$, and $CH_3SO_4^-$ with $Cl^-$ being particularly preferred. Alkyl groups can be straight or branched chained and alkyl and aryl groups can be substituted by non-interfering substituents that do not obstruct with the functionality of the polymers.

The cationic quaternary ammonium polymer can be prepared in an aqueous medium and form an hydrogel in situ or can be prepared in an aqueous medium, dried and converted into a powder which can then be reconstituted in aqueous media as a hydrogel.

The polymer is prepared by the polymerization of an acrylic acid monomer according to following Formula II:

FORMULA II

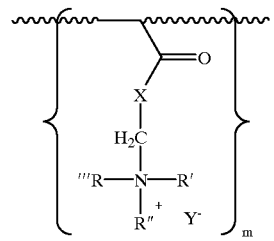

where n, R', R" and R'", X, $Y^-$ have the meanings given above in Formula I. Polymerization is brought about by methods known in the art such as free radical curing with an initiator induced polymerization in the presence of water by ultra-violet curing and a multi-functional cross-linking agent or by anionic 1,2 alkoxy anion induced polymerization.

The cationic quaternary ammonium polymers of this invention possess inherent microbiocidal properties and are absorbent and non-irritating to the skin or open wounds. The absorbency of the hydrogel means that, when applied as a wound dressing, fewer dressing changes are necessary, the wound heals faster and a moist healing environment is maintained. The polymers are radiation tolerant and can be sterilized by such means. Because the polymers are inherently microbiocidal, the wound is retained in a sterile environment to promote healing. Further, because the polymers are polycationic, it is possible that healing is accelerated because blood clotting is promoted due to the cationic polymer neutralizing polyanionic clotting inhibitors such as the naturally occurring anionic polysaccharide heparin.

The hydrogels are preferably prepared with a physical support structure to better retain the hydrogel over a wound. This physical support structure may be in the form an occlusive device having an impermeable backing, i.e. a patch. Since hydrogel is both inherently adhesive as well as antimicrobial, the use of more permanent adhesives may or may not be beneficial. The hydrogel can also be formed around a web or fibril support and fashioned by cutting into suitable sizes in both surface area and depth, i.e. sheets, strips, squares, circles, ovals, etc.

DETAILED DESCRIPTION OF THE INVENTION

The cationic quaternary amine polyacrylate gels of the invention are able to absorb significant amounts of fluid or exudate emanating from a wound or other skin surface abrasion. It is known that the accumulation of excess wound exudates is detrimental to healing and provides a fertile site for the growth of bacteria which further inhibits the healing process. Due to the absorbency of the hydrogels, the change of wound dressings can occur less frequently and still retain a sterile environment. Or, in the alternative, the wound dressing can be changed as needed if exudate production is high.

The cationic hydrogels maintain the wound in a moist condition which not only facilitates healing but also enhances the cosmetic appearance of the wound as it heals.

As previously noted, in order to maintain or promote sterility and enhance healing, an external antibiotic or other disinfectant has been added to prior art hydrogels and/or wound dressings. While such external antibiotics may still be added if it is deemed necessary, the inherent antimicrobial properties of the present hydrogels may make the additions of such external additives unnecessary. As will be seen, the antimicrobial properties of the hydrogels of this invention are effective agents against a wide range of microbes.

Another distinct advantage of the cationic quaternary amine polyacrylate hydrogels is sterilization. Suppliers of dressings generally place them in a sealed environment in a sterile condition. Because hydrogels are absorptive to steam and other sterilization agents, such as ethylene oxide, they cannot be sterilized by such means and the use of radiation is inimical to the stability of many prior art gels due to free radical degradation. The hydrogels of the present invention can be irradiated and sealed without adverse affects to the stability, adhesivity or antimicrobial properties of the hydrogel. Due to the ability of the polycationic hydrogels to be sterilized by radiation, they do not have to be formed or packaged in a "clean room" or sterile environment.

As noted in co-pending application Ser. No. 08/738,651 referenced above (issued Sep. 1, 1998 as U.S. Pat. No. 5,800,685), cationic quaternary amine polyacrylate hydrogels are good electrical conductors and can be formulated for use as electrodes in medical devices because they contact the skin with sufficient wetness and adhesive properties to allow passage of electrical current without substantially adversely affecting either the hydrogel or the skin.

When used as conductive adhesive hydrogels, high amounts of an electrical conductivity enhancer, such as potassium chloride, are generally added to the formulation. In the present invention, salt solutions of sodium or potassium chloride, at lower concentrations, may be present as polymerization enhancers in the formation of the hydrogels.

When using the cationic hydrogels as wound dressings, the gel may also contain a buffer system to help prevent discoloration and/or hydrolysis of the hydrogels, and/or improve their shelf-life. Other additives may also be added to the hydrogels either before or after curing (i.e. pharmaceuticals, humectants, plasticizers, etc.). The appropriateness of such additives is generally dependent upon which dressings are to be formulated and applied to a wound.

In addition to the absorbency of exudate and the inherent antimicrobial properties, there are other properties that make the present cationic acrylate hydrogels beneficial as wound dressings. They possess excellent physical characteristics in adhesiveness in that they both adhere to the skin when applied but are readily removable from the skin without leaving any gel residue. Also, when compared to prior hydrogels, the present cationic acrylate hydrogels are effective over a wide range of hydration. In other words, the gel may contain as little as 15 or as much as 95% by weight of the cationic polyacrylate. Preferably, the hydrogel will contain between about 61 to 90% by weight of the polyacrylate polymer with ranges of between about 65 to 75% by weight being particularly preferred. Even at the higher solids content of the polyacrylate polymer, the hydrogels are relatively non-irritating to the wound or skin surface.

The preferred chemical formula for cationic quaternary amine polyacrylates suitable for the present invention is shown in Formula I above. The quaternary amine containing acrylic acid ester or amide monomers that may be used for the polymerization process are shown in Formula II. The preferred method for making such cationic acrylates suitable for the present invention is described below.

Generally, the polymerization process will proceed in an aqueous solution such that the hydrogel formed will contain the solids content mentioned above with the balance being water or other additives as also mentioned above. If desired, the hydrogel may also include sufficient buffer to maintain the pH of the hydrogel in any desired pH range.

Examples of specific quaternary amine cationic acrylate ester or amide monomers that may be polymerized are shown in following Formulas III, IV, V and IV.

FORMULA III

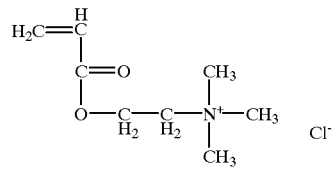

Formula III shows acryloyloxyethyltrimethyl ammonium chloride which is available from CPS Chemical Co.

FORMULA IV

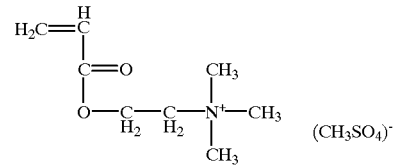

Formula IV shows acryloyloxyethyltrimethyl ammonium methyl sulfate which is available from Allied Colloid Co.

FORMULA V

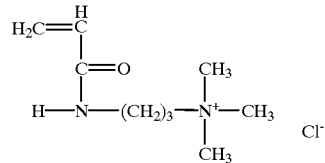

Formula V shows acrylamidopropyltrimethyl ammonium chloride which is available from Stockhausen (Germany).

FORMULA VI

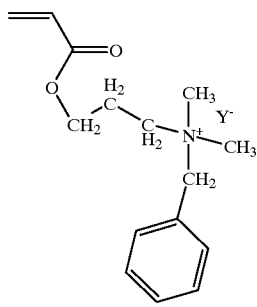

Formula VI shows acryloxyethyldimethylbenzyl ammonium chloride which is available from Elf Atochem.

The preferred process for making cationic quaternary amine polyacrylate hydrogels from one or more of these specific monomers is described in detail below.

The cationic quaternary amine polyacrylate hydrogels are preferably formed by in situ free radical polymerization of a water soluble monomer (such as those shown above) in the presence of water, preferably by ultra-violet curing with initiator(s) and multi-functional cross-linking agent(s). For example, an appropriate acrylate monomer (as shown in Formula III), water, optional additional polymerization enhancer (e.g. salt, for example, sodium chloride, potassium chloride, etc.), initiator or catalyst (e.g. α-hydroxy-1,α-dimethylacetophenone in DMSO, etc.), and a multi-functional cross-linker (e.g. methylene-bis-acrylamide, etc.) are combined, placed in a mold, and exposed to ultraviolet radiation as is known in the art. The resultant cationic quaternary amine polyacrylate hydrogel formed is somewhat clear in color, viscous, and tacky to the touch. The hydrogel tends to be sufficiently adhesive to a subject's skin for purposes of wound dressing, yet sufficiently cohesive to be is easily removable from the subject's skin and separable from itself.

As mentioned above, the present hydrogels may include a buffer system to help control the pH, help prevent discoloration, and/or help prevent breakdown due to the extended presence of water (i.e. help prevent hydrolysis). Buffers, if any, are preferably added to the mixture prior to curing. Suitable buffers include, for example, but are not limited to, sodium potassium tartarate, and/or sodium phosphate monobasic, both of which are commercially readily available from, for example, Aldrich Chemical Co., IN. The use of a buffer system with the present hydrogel is preferred to provide the hydrogel with a commercially suitable shelf-life (i.e. a shelf-life of over one year) without discoloration.

As is also mentioned above, other additives may be included in the present hydrogels either before or after curing (i.e. pharmaceuticals such as antibiotics, disinfectants and the like, humectants, plasticizers, etc.). The appropriateness of such additives is generally dependent upon the intended end use of the particular hydrogel as a wound dressing.

As is mentioned above, initiators are preferably used in the polymerization of the present hydrogels. Examples of initiators which may be used include, for example, IRGACURE® 184 (1-hydroxycyclohexyl phenyl ketone), and DAROCURE® 1173 (α-hydroxy-1, αdimethylacetophenone) which are both commercially available from Ciba-Geigy Corp. These UV catalysts are preferred because they are non-yellowing. Other initiators which maintain the preferred water-white and water-clear appearance of the hydrogels are preferred. However, additional examples of initiators (which may be photo initiators or thermal initiators) may include benzoyl peroxide, azo-bis-isobutyro-nitrile, di-t-butyl peroxide, bromyl peroxide, cumyl peroxide, lauroyl peroxide, isopropyl percarbonate, methylethyl ketone peroxide, cyclohexane peroxide, t-butylhydroperoxide, di-t-amyl peroxide, dicumyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), acetophenones (such as acetophenone, trichloroacetophenone, 2,2-diethoxyacetophenone, p-t-butyltrichloro-acetophenone, 2,2-dimethoxy-2-phenyl-acetophenone, and p-dimethylaminoacetophenone), thioxanthones (such as xanthone, thioxanthone, 2-chlorothioxanthone, and 2-isopropyl thioxanthone), benzyl 2-ethyl anthraquinone, methylbenzoyl formate, 2-hydroxy-2-methyl-1-phenyl propane-1-one, 2-hydroxy-4'-isopropyl-2-methyl propiophenone, e-hydroxy ketone, tetramethyl thiuram monosulfide, allyl diazonium salt, and combination of camphorquinone and ethyl 4-(N,N-dimethylamino) benzoate. Other initiators may be found in, for example, Berner, et al., "Photo Initiators—An Overview," J. Radiation Curing (April 1979), pp. 2–9.

The amount of initiator is preferably within the range of about 0.02 to 2.0% by weight based on total amount of monomer, and more preferably within the range of about 0.05 to 0.5% by weight based on total amount of monomer.

UV curing parameters to achieve desired polymer properties are well known to those skilled in the art. An initiator for the present purposes tends to operate by absorbing select wavelengths of UV light, and breaking down into free radicals to initiate polymerization. The wavelengths and curing area set the style of UV bulb used in the curing process. Inhibition of polymerization due to dissolved oxygen, monomer preservatives, or other components may be overcome by changing the power, by pulsing, and/or by using catalyst accelerators. The amount of residual monomer (after polymerization) is preferred to be less than about 3% for good biocompatability.

As is also noted above, cross-linking agents are preferably used to cross-link the present cationic polyacrylate hydrogels. Examples of multi-functional cross-linking agents which may be used are methylene-bis-acrylamide (MBA) and diethylene glycol diacrylate, which are both commercially available from Polysciences, Inc., Warrington, Pa. Additional examples of cross-linking agents which may be acceptable for use in the present invention include ethylene glycol diacrylate, triethylene glycol-bis-methacrylate, ethylene glycol-bis-methacrylate, ethylene glycol-dimethacrylate, bisacrylamide, triethyleneglycol-bis-acrylate, 3,3'-ethylidene-bis (N-vinyl-2-pyrrolidone), trimethylolpropate trimethacrylate, glycerol trimethacrylate, polyethylene glycol dimethacrylate, and other polyacrylate and polymethacrylate esters.

The amount of cross-linking agent used is preferably within the range of about 0.02 to 2.0% by weight based on total amount of monomer, and more preferably within the range of about 0.05 to 0.5% by weight based on total amount of monomer.

There follows specific exemplary embodiments of cationic quaternary amine acrylate hydrogels of the present invention.

In each of the following examples the acrylate quaternary amine monomer utilized was 80% acryloyloxyethyltrimethyl ammonium chloride in water (AAC), the cross-linking solution was 1% methylene-bis-acrylamide in water (MBA), the catalyst was 0.01% α-hydroxy-1,α-dimethylacetophenone in DMSO (DAROCURE® 1173).

EXAMPLE 1

| Ingredients: | Amount: |
|---|---|
| AAC | 122 grams |
| 2% Saline | 80 grams |
| 1% MBA | 20 grams |
| Darocure 1173 | 800 μl |

These materials were mixed in the order given and placed under a suitable UV curing system, as described above, and cured according to processes well known in the art.

The resultant gel was transparent, had a light tack and had a solids content of 61% by weight.

EXAMPLE 2

| Ingredients: | Amount: |
|---|---|
| AAC | 61 grams |
| Water | 40 grams |
| 1% MBA | 10 grams |
| Darocure 1173 | 400 μl |

The resultant gel had a solids content of 61% by weight and is similar to Example 1, except that the saline solution was replaced by water. The polymerization process was the same as were the properties of the gel.

EXAMPLE 3

| Ingredients: | Amount: |
|---|---|
| AAC | 140 grams |
| 2% Saline | 60 grams |
| 1% MBA | 20 grams |
| Darocure 1173 | 800 μl |

The procedure of Example 1 was followed and the resultant transparent gel had a light tack and a solids content of 70% by weight.

EXAMPLE 4

| Ingredients: | Amount: |
|---|---|
| AAC | 70 grams |
| Water | 30 grams |
| 1% MBA | 10 grams |
| Darocure 1173 | 400 μl |

The resultant transparent gel had a light tack and a solids content of 70% by weight. This example is similar to Example 3 except that the saline solution was replaced by water. The polymerization process was the same.

EXAMPLE 5

| Ingredients: | Amount: |
|---|---|
| AAC | 70 grams |
| Water | 30 grams |
| 1% MBA | 5 grams |
| Darocure 1173 | 400 μl |

The resultant gel had a solids content of 70% by weight and is similar to Example 5, except that the MBA crosslinker was cut in half. The polymerization process was the same and the gel was essentially clear with a light tack.

EXAMPLE 6

| Ingredients: | Amount: |
|---|---|
| AAC | 160 grams |
| 2% Saline | 40 grams |
| 1% MBA | 20 grams |
| Darocure 1173 | 800 μl |

The procedure of Example 1 was followed and the resultant transparent gel had a light tack and a solids content of 80% by weight.

EXAMPLE 7

| Ingredients: | Amount: |
|---|---|
| AAC | 80 grams |
| Water | 20 grams |
| 1% MBA | 10 grams |
| Darocure 1173 | 400 μl |

The resultant gel had a solids content of 80% by weight and is similar to Example 6 except that the saline solution was replaced by water. The polymerization process was the same as were the physical properties of the gel.

EXAMPLE 8

| Ingredients: | Amount: |
|---|---|
| AAC | 80 grams |
| Water | 20 grams |
| 1% MBA | 5 grams |
| Darocure 1173 | 400 μl |

The resultant gel had a solids content of 80% by weight and is similar to Example 7 except that the MBA crosslinker was cut in half. The polymerization process was the same as were the physical properties of the gel.

EXAMPLE 9

| Ingredients: | Amount: |
| --- | --- |
| AAC | 90 grams |
| Water | 10 grams |
| 1% MBA | 10 grams |
| Darocure 1173 | 400 μl |

The gel was prepared as in Example 1. The resultant transparent gel had a light tack and a solids content of 90% by weight.

EXAMPLE 10

| Ingredients: | Amount: |
| --- | --- |
| AAC | 90 grams |
| 2% Saline | 10 grams |
| 1% MBA | 5 grams |
| Darocure 1173 | 400 μl |

The resultant gel had a solids content of 90% by weight and is similar to Example 9 except that the water was replaced by 2% saline and the MBA crosslinker was cut in half. The polymerization process was the same and the gel properties were similar.

EXAMPLE 11

| Ingredients: | Amount: |
| --- | --- |
| AAC | 180 grams |
| 2% Saline | 20 grams |
| 1% MBA | 20 grams |
| Darocure 1173 | 800 μl |

The resultant gel had a solids content of 90% by weight and is similar to Example 10 except that the MBA crosslinker was doubled. The polymerization process was the same as were the gel properties.

EXAMPLE 12

The gel of Example 11 was screened for antimicrobial activity using a procedure that was an adaption of the Kirby-Bauer method of testing antibiotics.

The following organisms were transferred to soybean casein digest agar (SCDA), and incubated at 37±2° C. for 24–28 hours:

*Pseudomonas aeruginosa,* ATCC #9027

*Eschericia coli,* ATCC #8739

*Klebsiella pneumoniae,* ATCC #4352

*Staphylococcus aureus,* ATCC # 6538

*Enterococcus* (Streptococcus) *faecalis,* ATCC #19433

*Candida albicans,* ATCC #10231

The test organisms were harvested using 0.9% saline. Each culture was vortexed vigorously to break up clumps. The titer of each suspension was adjusted to approximately $10^6$ colony formings units per mL (CFU/mL). The titer of the organism suspensions were confirmed using plate count techniques.

On each test plate, a confluent lawn of organism was prepared by first wetting a sterile cotton swab with the test organism suspension, then streaking on a Muller-Hinton agar (MHAG) plate in three directions with a final sweep around the outside edge of the plate. A total of seven plates were prepared for each set of samples. An additional plate was prepared and incubated as a positive control. A negative sample control and media control were also included.

The gel samples were cut into uniform pieces approximately 5 mm square. Each sample was tested on seven different agar plates. The plates were incubated at 37±2° C. until a confluent lawn of the test organism was apparent. The plates were refrigerated at 2–8° C. over the weekend until they could be measured.

Average zones of inhibition of each sample and test organism are reported in Table 1.

TABLE 1

| AVERAGE ZONE OF INHIBITION IN MILLIMETERS | | | |
| --- | --- | --- | --- |
| Test Organism | Group A | Group B | Group C |
| *Escherichia coli* | 18.1 | 16.3 | 15.4 |
| *Pseudomonas aeruginosa* | 17.8 | 15.3 | 20.4 |
| *Klebsiella pneumoniae* | 14.4 | 15.1 | 14.6 |
| *Staphylococcus aureus* | 16.4 | 16.7 | 15.6 |
| *Enterococcus faecalis* | 13.7 | 16.9 | 14.2 |
| *Candida albicans* | 0 | 0 | 0 |

The inoculating titer of each organism is found in Table 2.

TABLE 2

| INOCULUM TITERS | |
| --- | --- |
| Test Organism | Inoculum Titer |
| *Escherichia coli* | $1.3 \times 10^6$ cfu/mL |
| *Pseudomonas aeruginosa* | $5.5 \times 10^6$ cfu/mL |
| *Klebsiella pneumoniae* | $1.2 \times 10^6$ cfu/mL |
| *Staphylococcus aureus* | $2.5 \times 10^6$ cfu/mL |
| *Enterococcus faecalis* | $1.3 \times 10^6$ cfu/mL |
| *Candida albicans* | $3.1 \times 10^6$ cfu/mL |

It is evident that, except for *Candida albicans,* the gel of Example 11 showed significant antimicrobial properties as determined by the average zone of inhibition. Although no zones of inhibition were observed on the *Candida albicans* plates, there was significantly less growth surrounding these test samples indicating some antimicrobial activity.

EXAMPLE 13

To determine whether the gels of the present invention exhibited any adverse effects on scarified areas of human skin, five test samples were selected and tested. The tests were conducted by an independent testing laboratory using a standard Chamber Scarification Test procedure. Only a summary of the procedure is given in this example.

The following hydrogels were tested: Sample A (the gel of Example 1), Sample B (the gel of Example 5), Sample C (the gel of Example 6), Sample D (the gel of Example 11) and Sample E (the gel of Example 5 having a minor amount of povidone-iodine, Betadine® added).

The gels were formed into circular pledgets 2 cm in diameter for insertion into a chamber well. Control patches of clean webril material was stamped out and moistened with a control material for comparison purposes.

Ten volunteers were used in the tests. A distinct site of the surface of the forearm of each test subject was selected and designated for contact with each of Samples A–E and controls. The location of the site allocated to one test material as compared to the others varied from subject to subject.

The skin of each volunteer was cleansed with alcohol and each site outlined. The skin of each site was scratched with the sharp beveled edge of a 30-gauge needle. A newly opened sterile needle was used for each participant. Three strokes were made horizontally and three vertically in a cross-hatch formation. Just enough pressure was applied to the needle to cleave the epidermis without eliciting frank capillary bleeding. Each site was then covered with a chamber containing webril pads that had been moistened with 0.1 ml of sterile physiological saline. The chambers were moored tightly to the sites with wide strips of Hypifix® Tape. After four hours, the chambers were removed and the scarified sites were examined and graded for adverse changes. These graded sites were then used as a baseline for determining the effects of the hydrogel samples on the sites.

After the baseline value had been established, and using aseptic techniques, the protective covering over the prepared sample chambers was peeled off and the exposed gel pledget was placed directly on the scarified site. The pledget was then covered with a chamber device and moored in place with Hypafix® Tape.

The test sites on each volunteer were examined daily and graded and the pledget sample was again replaced until being examined the following day.

After seventy two hours the test was terminated and the data on each test subject compiled and averaged for each test sample. Each site was scored as follows: 1 =No scarification marks or erythema visible; 0.5 =scarification marks visible but no erythema present; 1 =faint erythema along the scarification marks; 2 =moderate to intense erythema adjacent to the scratch marks; areas between scratch marks unaffected; 3 =confluent, severe erythema filling areas between scratch marks; 4 =severe erythema associated with pustules or blisters.

A mean score of 0.0 to 0.49 was deemed to indicate very low irritating potential. A mean score of 0.5 to 1.49 indicated low irritating potential. A mean score of 1.5 to 2.49 indicated moderate irritating potential. A mean score of 2.5 to 4.0 indicated high irritating potential.

The results are given below with the physiological saline being used as the baseline on which to grade the other samples.

TABLE 3

| | MEAN SCORES | | | |
|---|---|---|---|---|
| | 0 Hour | 24 Hour | 48 Hour | 72 Hour |
| Control | 0.65 | 0.55 | 0.55 | 0.50 |
| Sample A[a] | 0.70 | 0.75 | 1.20 | 0.70 |
| Sample A[b] | −0.05 | −0.05 | −0.05 | −0.05 |
| Sample A[c] | 0.65 | 0.70 | 1.15 | 0.65 |
| Sample B[a] | 0.60 | 0.80 | 0.75 | 0.55 |
| Sample B[b] | +0.05 | +0.05 | +0.05 | +0.05 |
| Sample B[c] | 0.65 | 0.85 | 0.80 | 0.60 |
| Sample C[a] | 0.65 | 0.55 | 0.65 | 0.60 |
| Sample C[b] | 0.00 | 0.00 | 0.00 | 0.00 |
| Sample C[c] | 0.65 | 0.55 | 0.65 | 0.60 |
| Sample D[a] | 0.60 | 0.60 | 0.60 | 0.50 |
| Sample D[b] | +0.05 | +0.05 | +0.05 | +0.05 |
| Sample D[c] | 0.65 | 0.65 | 0.65 | 0.55 |
| Sample E[a] | 0.65 | 0.85 | 0.90 | 0.65 |

TABLE 3-continued

| | MEAN SCORES | | | |
|---|---|---|---|---|
| | 0 Hour | 24 Hour | 48 Hour | 72 Hour |
| Sample E[b] | 0.00 | 0.00 | 0.00 | 0.00 |
| Sample E[c] | 0.65 | 0.85 | 0.90 | 0.65 |

[a]Mean score
[b]Adjustment value [Baseline control score (0 Hour) minus baseline sample score (0 hour)]
[c]Adjusted mean score (Adjustment value plus sample mean score)

It can be seen from the above that all samples A–E are not significantly different from the control in irritation potential, i.e. all, including the saline control, rank in the "low" category. While there was not sufficient data collected to determine the degree of wound healing attributable to the samples, many of the test subjects commented that their scarifications were less painful after the dressings containing Samples A–E were applied. In other words, when samples A–E were applied to the scarifications there was a soothing effect observed.

The above description will enable one skilled in the art to make and use cationic quaternary amine polyacrylate hydrogels as wound dressings. The description is not intended to be an exhaustive statement of all embodiments of the invention. Neither are all cationic quaternary amine polyacrylate polymers, which may be prepared, specifically shown. It will be apparent to one skilled in the art that various modifications may be made without departing from the scope of the invention which is limited only by the following claims and their functional equivalents.

What is claimed is:

1. A method for treating a wound with an inherently antimicrobial dressing comprising the steps of:

(a) providing a hydrogel containing from about 15 to 95 percent by weight of an inherently antimicrobial cationic quaternary amine acrylate polymer of the formula:

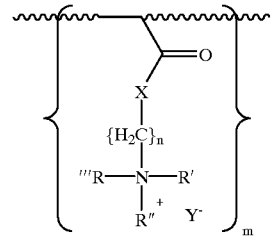

wherein n is an integer of 2 to 3; R', R" and R'" are independently selected from the group consisting of H, $C_1$ to $C_{16}$ alkyl, aryl, arylamine, alkylamine, alkaryl and aralkyl; X is selected from the group consisting of O and NH; $Y^-$ is an acceptable anionic counterion to the $N^+$ of the quaternary amine and m is an integer greater than 50,000 in a form suitable to cover the wound;

(b) applying said wound dressing to said wound whereby said dressing enhances the serility of the wound environment, absorbs exudate from said wound and retains said wound in a moist condition.

2. A method according to claim 1 wherein said wound dressing is affixed to device for the dressing of wounds.

3. A method according to claim 2 wherein said device comprising a substrate of a fibrous sheet material embedded in said hydrogel and wherein said hydrogel has opposing surfaces at least one of which is adapted to cover and be in contact with a wound.

4. A method according to claim 2 wherein said device is an occlusive structure and wherein said hydrogel has opposing surfaces such that one surface of said hydrogel is affixed to one surface of said occlusive structure with said opposing surface being adapted to cover and be in contact with a wound.

5. A method according to claim 3 or 4 wherein, in the polymer forming the hydrogel, R', R" and R'" are independently selected from the group consisting of H, $C_1$ to $C_8$ alkyl, phenyl, tolyl and benzyl.

6. A method according to claim 5 wherein, in the polymer, R', R" are methyl and R'" is benzyl.

7. A method according to claim 5 wherein, in the polymer, R', R" and R'" are methyl.

8. A method according to claim 7 wherein, in the polymer, X is O.

9. A method according to claim 7 wherein, in the polymer, X is NH.

10. A method according to claim 7 wherein, in the polymer, $Y^-$ is a member selected from the group consisting of $Cl^-$, $Br^-$, $HSO_4^-$, and $CH_3SO_4^-$.

11. A method according to claim 10 wherein, in the polymer, $Y^-$ is $Cl^-$.

12. A method according to claim 7 wherein, in the polymer, n is 2.

13. A method according to claim 7 wherein, in the polymer, n is 3.

14. A method according to claim 2 wherein the hydrogel contains between about 61 and 90% by weight of said cationic quaternary amine polyacrylate polymer.

15. A method according to claim 14 wherein the hydrogel contains between about 65 and 75% by weight of said cationic quaternary amine polyacrylate polymer.

* * * * *